(12) United States Patent
Heng et al.

(10) Patent No.: US 8,138,386 B2
(45) Date of Patent: Mar. 20, 2012

(54) METHOD FOR CONVERTING HYDROCARBONS WITH ZEOLITE SHAPED CATALYST

(75) Inventors: Phala Heng, Yokohama (JP); Teruo Muraishi, Yokohama (JP); Michiaki Umeno, Chiba (JP); Hirokazu Ikenaga, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 221 days.

(21) Appl. No.: 12/531,535

(22) PCT Filed: Mar. 17, 2008

(86) PCT No.: PCT/JP2008/054862
§ 371 (c)(1),
(2), (4) Date: Sep. 16, 2009

(87) PCT Pub. No.: WO2008/114771
PCT Pub. Date: Sep. 25, 2008

(65) Prior Publication Data
US 2010/0063341 A1    Mar. 11, 2010

(30) Foreign Application Priority Data
Mar. 20, 2007  (JP) .................. 2007-072979

(51) Int. Cl.
*C07C 4/06*  (2006.01)
(52) U.S. Cl. ......... 585/653; 585/648; 208/113; 208/118
(58) Field of Classification Search ........................ None
See application file for complete search history.

(56) References Cited

U.S. PATENT DOCUMENTS

| | | | | |
|---|---|---|---|---|
| 5,053,374 A * | 10/1991 | Absil et al. | ...................... | 502/64 |
| 5,120,893 A * | 6/1992 | Gabriel et al. | ................. | 585/653 |
| 5,387,564 A * | 2/1995 | Takeuchi et al. | ................. | 502/62 |
| 6,491,861 B1 * | 12/2002 | Grosch et al. | ................. | 264/628 |
| 6,680,271 B1 * | 1/2004 | Heindl et al. | ................... | 502/64 |
| 7,317,133 B2 * | 1/2008 | Vora et al. | ...................... | 585/327 |
| 7,375,257 B2 * | 5/2008 | Dath et al. | ..................... | 585/653 |
| 2004/0064008 A1 * | 4/2004 | Maurer et al. | ................ | 585/640 |

FOREIGN PATENT DOCUMENTS

| | | |
|---|---|---|
| EP | 0592050 | 4/1996 |
| JP | 59059741 | 4/1984 |
| JP | 6126509 | 2/1986 |
| JP | 61155216 | 7/1986 |
| JP | 61242911 | 10/1986 |
| JP | 02157118 | 6/1990 |
| JP | 03140286 | 6/1991 |
| JP | 04346839 | 12/1992 |
| JP | 06211517 | 8/1994 |
| JP | 10087322 | 4/1998 |
| JP | 2002079087 | 3/2002 |
| JP | 2002136871 | 5/2002 |
| JP | 2003510181 | 3/2003 |
| JP | 2004169011 | 6/2004 |
| JP | 2005-270851 | 10/2005 |

OTHER PUBLICATIONS

International Search Report for PCT/JP2008/054862 dated May 27, 2008.
Book of Abstracts, 229th ACS National Meeting, Mar. 13-17, 2005, San Diego, CA.
J. Weitkamp et al., Catalysis and Zeolites, Fundamentals and Applications, 1999, pp. 127-155.

* cited by examiner

*Primary Examiner* — Tam M Nguyen
(74) *Attorney, Agent, or Firm* — Rankin, Hill & Clark, LLP

(57) ABSTRACT

The invention provides methods for converting hydrocarbons as starting material by industrial fixed-bed reaction processes with a zeolite shaped catalyst which has a low content of inorganic binder and a high pore volume and which shows high catalytic activity, long catalyst life and high crushing strength. A zeolite shaped catalyst used in the methods of the invention includes zeolite and an inorganic binder and is obtained by kneading zeolite, a starting material of an inorganic binder, shaping auxiliary(ies), organic polymer particles having an average diameter of 0.1 to 6 µm and water into a kneaded product, and extruding, drying and calcining the kneaded product; and the zeolite shaped catalyst has a zeolite component content of not less than 60 wt % relative to the total weight, a pore volume of 0.4 to 1.0 ml/g, a half-volume pore diameter of 80 to 500 nm and a crushing strength of not less than 0.9 kg.

10 Claims, No Drawings

METHOD FOR CONVERTING HYDROCARBONS WITH ZEOLITE SHAPED CATALYST

FIELD OF THE INVENTION

The present invention relates to methods for converting hydrocarbons with a zeolite shaped catalyst. In more detail, the invention relates to methods for converting hydrocarbons as starting material by reactions such as fixed-bed reactions with use of a zeolite shaped catalyst having high catalytic activity, long catalyst life and high crushing strength.

BACKGROUND OF THE INVENTION

Zeolites are powdery crystalline substances that are widely used as catalysts in industrial processes.

To achieve a certain level of crushing strength for industrial use, zeolite power is integrated through a binding substance called a binder and is shaped into a size that is easy to handle. However, such shaped catalysts generally have lower performance than they show in the original powder form. This reduction in performance is probably due to alterations of or interferences to the catalytically active sites in the zeolites by the interaction or chemical bonds with the binders. Further, starting material and products are diffused more slowly in the shaped catalysts than in vacuum or organic solvents. As a result, the supply rate of starting material to the catalytically active sites cannot keep up with the reaction rate. In addition, the product is caused to stay longer in the catalyst and consequently side reactions are accelerated, a state called diffusion-limited state. In particular, the limited diffusion results in accelerated accumulation of cokes in the case of highly active catalysts or under high temperature or high pressure where the reaction rate is high. As a result, the shaped catalysts drastically reduce their activity and life, which are the most important properties in the use of catalysts. Further, the binders sometimes work as catalysts to cause side reactions.

Countermeasures to minimize the reduction in performance of the zeolite shaped catalysts include reducing the usage amounts of binders and increasing the pore volume of the shaped catalysts. The binders are selected from compounds that are inactive in reactions to be catalyzed by the shaped catalysts and do not deteriorate the reactivity of the zeolites. Decreasing the usage amount of binders reduces the crushing strength of the shaped catalysts and makes the shaping difficult. Increasing the pore volume reduces the crushing strength of the shaped catalysts. Further, shaping properties are another problem that should be solved to obtain shaped catalysts having desired properties. For example, extrusion methods entail that a mixture of zeolite, a binder material, water and a shaping auxiliary has an appropriate viscosity for the mixture to be shapeable with an extruder. The mixture cannot be extruded with an excessively high viscosity and cannot be shaped with an excessively low viscosity.

The shaping auxiliaries are for example thickening agents, surfactants, water retention agents, plasticizers and organic binders. Selection of the shaping auxiliaries is difficult because not only shaping properties but also freeness of adverse effects on performance of the shaped catalysts should be considered.

A large number of methods for solving the above problems have been disclosed.

For example, Patent Documents 1 to 4 disclose methods for forming adsorbents or catalysts. These patent documents involve carboxymethyl celluloses as shaping auxiliaries, and binders used therein are inorganic compounds which are bound with zeolites relatively easily, such as acid clay, Kibushi clay, sepiolite, attapulgite and kaolin. These inorganic binders contain large amounts of impurities other than alumina components and the like and can deteriorate the catalytic performance of zeolite in some reactions. Accordingly, they should be removed from the shaped catalysts in a separate step and the production costs are increased.

Patent Document 5 discloses a process of producing a shaped catalyst from a siliceous solid and zeolite in the presence of an alkali metal compound. In the working examples disclosed therein, high crushing strength (12.7 kg/cm) and high pore volume (0.615 cc/g) are obtained with the pore diameters concentrated in 200 to 600 Å (20 to 60 nm) when the content of the silica binder in ZSM-5 zeolite shaped catalyst is relatively low at 35.5%. According to this process, siliceous solids are used as binders and thereby the zeolite shaped catalysts are free from substances that will deteriorate the catalytic performance. However, the crystallinity of the aluminosilicate zeolite can be reduced in the presence of alkali metal compounds, possibly resulting in lower catalytic performance. Further, treatments with ammonium nitrate and nitric acid are required in a later stage of the catalyst production to remove the alkali metals. Thus, this process is not economical.

Patent Documents 6 to 8 disclose extrusion methods for shaping zeolites wherein the use of alkali metals is eliminated by using amine compounds as shaping auxiliaries. Silica sol is used as a silica binder material that does not deteriorate the performance of the zeolite catalysts. This method has been shown to maintain substantially intact the crystallinity of zeolite in the shaped catalysts and to provide high crushing strength of the shaped catalysts. However, according to the working examples disclosed therein, the content of silica binder in the shaped catalysts is high ranging from 40 to 50 wt %, and great reduction in shaped catalyst performance is inevitable.

Patent Documents 9 and 10 disclose processes for producing titanium oxide-supported catalysts capable of decomposing and removing harmful components in incinerator exhaust gases, in which processes easily thermally decomposable substances such as acetal resins, acrylic resins, polyester resins and methacrylic acids are used as porosifiers whereby pore sizes in the range of 300 to 450 nm are created. In these processes, the porosifiers are decomposed during the production. According to the working examples disclosed therein, resins having a particle diameter of 3 μm should be used in order to obtain pore sizes in the above range. That is, the porosifier particle diameters are greatly different from the target pore sizes. Therefore, it is expected that controlling the pore volumes or pore diameters will be difficult and creating pores in uniform sizes will be even more difficult.

As described above, the use of carboxymethyl celluloses as shaping auxiliaries in combination with binders such as kaolinite and acid clay which are easily bound with zeolites can result in deteriorated performance of the shaped catalysts. The silica binders do not greatly reduce the shaped catalyst performance but do not have good shaping properties with zeolites. By the use of alkali metals in extrusion material mixtures, the mixtures can be extruded to give shaped catalysts having a sufficiently high pore volume and high crushing strength. However, it also entails a step for removing large amounts of alkali metals and adds costs; further, controlling properties of the shaped catalysts is difficult. The use of amine compounds as shaping auxiliaries allows for extrusion shaping under a weakly alkaline atmosphere. However, the binder content has to be increased to a certain level in order to obtain sufficient crushing strength, and consequently the reduction in performance such as catalytic activity and life of the shaped catalysts cannot be avoided.

Patent Document 1: JP-A-S61-155216
Patent Document 2: JP-A-S61-242911
Patent Document 3: JP-A-H02-157118
Patent Document 4: JP-A-H10-087322
Patent Document 5: JP-A-S61-026509
Patent Document 6: JP-A-H04-346839
Patent Document 7: JP-A-H06-211517
Patent Document 8: JP-A-2003-510181
Patent Document 9: JP-A-2002-079087
Patent Document 10: JP-A-2002-136871

SUMMARY OF THE INVENTION

It is an object of the present invention to provide methods for converting hydrocarbons as starting material by industrial fixed-bed reaction processes with a zeolite shaped catalyst which has a low content of inorganic binders and a high pore volume and which shows high catalytic activity, long catalyst life and high crushing strength.

The present inventors diligently studied zeolite shaped catalysts and processes for the production thereof in order to achieve the above object. They have then found that zeolite shaped catalysts having a zeolite component content of not less than 60 wt %, a pore volume of 0.4 to 1.0 ml/g and a half-volume pore diameter of 80 to 500 nm have a high crushing strength of not less than 0.9 kg and can catalyze fixed-bed reactions of hydrocarbons as starting material. They have also developed processes for producing zeolite shaped catalysts having the above properties, which processes comprise kneading zeolite powder, starting material of an inorganic binder, shaping auxiliary(ies), organic polymer particles and water into an extrudable clay-like kneaded product, shaping the kneaded product by extrusion, and drying and calcining the shaped product.

It has been found that the shaped catalysts can catalyze industrial fixed-bed reactions of hydrocarbons as starting material without drastic reduction in catalytic activity and acceleration of coke generation compared to zeolites in the original powder form, whereby the above object has been accomplished.

As described hereinabove, reducing the usage amounts of inorganic binders or increasing the pore volume has been a conventional approach to prevent the deterioration in shaped catalyst performance. However, such approaches have eventually resulted in the lowering in shaped catalyst performance. The present inventors studied the causes of this lowered performance of the shaped catalysts, in particular focusing on the pore diameter distribution in the shaped catalysts according to mercury porosimetry. As a result, they have found that a satisfactory diffusion rate of materials is ensured with pores having at least a certain size, whereby reduced reaction rate and accelerated coke generation are both prevented. It has been also found that half-volume pore diameter is an effective index of an average distribution of pores in the shaped catalyst.

According to the production processes of the present invention, the present inventors have minimized the usage amount of shaping auxiliaries that irregularly influence the pore volume and pore diameter and have adopted organic polymer particles having an optimum particle diameter and a relatively narrow particle size distribution, whereby the formation of pores in the shaped catalyst can be controlled and the obtainable zeolite shaped catalysts achieve the foregoing properties. The present inventors have also invented methods for converting hydrocarbons with the zeolite shaped catalysts manufactured by the processes. The present invention has been thus completed.

The methods for converting hydrocarbons with zeolite shaped catalysts according to the invention include the following embodiments.

(1) A conversion method comprising catalytically cracking a hydrocarbon starting material containing olefins into olefins that are lower than the starting material with use of a zeolite shaped catalyst, the zeolite shaped catalyst being obtained by kneading zeolite powder, a starting material of an inorganic binder, shaping auxiliary(ies), organic polymer particles having an average diameter of 0.1 to 6 μm and water into a kneaded product, and extruding, drying and calcining the kneaded product.

(2) A conversion method comprising catalytically cracking hydrocarbon starting material containing olefins into olefins that are lower than the starting material with use of a zeolite shaped catalyst, the zeolite shaped catalyst comprising zeolite and an inorganic binder and having a zeolite component content of not less than 60 wt % relative to the total weight, a pore volume of 0.4 to 1.0 ml/g, a half-volume pore diameter of 80 to 500 nm and a crushing strength of not less than 0.9 kg.

(3) A conversion method comprising catalytically cracking hydrocarbon starting material containing olefins into olefins that are lower than the starting material with use of a zeolite shaped catalyst, the zeolite shaped catalyst comprising zeolite and an inorganic binder and being obtained by kneading zeolite powder, starting material of an inorganic binder, shaping auxiliary(ies), organic polymer particles having an average diameter of 0.1 to 6 μm and water into a kneaded product, and extruding, drying and calcining the kneaded product, the zeolite shaped catalyst having a zeolite component content of not less than 60 wt % relative to the total weight, a pore volume of 0.4 to 1.0 ml/g, a half-volume pore diameter of 80 to 500 nm and a crushing strength of not less than 0.9 kg.

(4) The conversion method as described in any one of (1) to (3), wherein the zeolite is MFI zeolite.

(5) The conversion method as described in any one of (1) to (3), wherein the content of the inorganic binder is not more than 40 wt % relative to the total weight of the zeolite shaped catalyst.

(6) The conversion method as described in any one of (1) to (3), wherein the inorganic binder is silica.

(7) The conversion method as described in (1) or (3), wherein the amounts are 100 parts by weight for the zeolite powder, 10 to 70 parts by weight for the inorganic binder material, not more than 15 parts by weight for the starting material of the inorganic binder, not more than 15 parts by weight for the shaping auxiliary(ies), 10 to 60 parts by weight for the organic polymer particles having an average diameter of 0.1 to 6 μm, and 20 to 60% for water relative to the total weight of the kneaded product.

(8) The conversion method as described in (1) or (3), wherein the zeolite powder is ammonium zeolite or alkaline zeolite.

(9) The conversion method as described in (1) or (3), wherein the starting material of the inorganic binder is a silica sol or a sodium silica sol.

(10) The conversion method as described in any one of (1) to (3), wherein the hydrocarbon starting material containing olefins contain at least one C4-12 olefin and 10 to 60 wt % of at least one C1-12 saturated hydrocarbon, wherein the olefins that are lower than the starting material are ethylene and propylene, and wherein the catalytic cracking temperature is in the range of 400 to 580° C.

(11) The conversion method as described in (10), wherein the catalytic cracking pressure is in the range of 0.05 to 2 MPa and the weight hourly space velocity (WHSV) of the hydrocarbon starting material per unit catalyst is in the range of 20 to 256 $hr^{-1}$.

ADVANTAGEOUS EFFECTS OF THE INVENTION

The zeolite shaped catalysts used in the hydrocarbon conversion methods of the invention have a low content of inorganic binders and a high pore volume but still ensure high crushing strength. Accordingly, the catalysts show high catalytic activity and long catalyst life in industrial fixed-bed reactions of hydrocarbons as starting material. The zeolite shaped catalysts used in the invention are obtained by kneading zeolite powder, starting material of an inorganic binder, shaping auxiliary(ies), organic polymer particles having an average diameter of 0.1 to 6 μm and water into a kneaded product, and extruding, drying and calcining the kneaded product. The zeolite shaped catalysts thus produced have a low content of inorganic binders and a high pore volume but still ensure high crushing strength, showing high catalytic activity and long catalyst life.

The zeolite shaped catalysts are suitably used in industrial fixed-bed reactions of hydrocarbons as starting material. In particular, the catalysts are suitably used to catalytically crack a hydrocarbon material containing at least one C4-12 olefin and 10 to 60 wt % of at least one C1-12 saturated hydrocarbon, into ethylene and propylene.

PREFERRED EMBODIMENTS OF THE INVENTION

The zeolite shaped catalysts in the invention contain zeolite and an inorganic binder, with the zeolite content being in the range of 60 to 90 wt %, preferably 65 to 88 wt %, and more preferably 70 to 85 wt %. The catalysts have a pore volume of 0.4 to 1.0 ml/g, preferably 0.5 to 0.8 ml/g, a half-volume pore diameter of 80 to 500 nm, preferably 80 to 400 nm, and a crushing strength of not less than 0.9 kg, preferably not less than 1.0 kg.

The present inventors have found surprising advantages that the zeolite shaped catalysts having the above properties are efficiently prevented from reduction in performance compared to the zeolites in the original powder form, and have crushing strength enough for use in fixed-bed reactions of hydrocarbons as starting material. If the pore volume is less than 0.4 ml/g, the catalytic performance is lowered and the coke generation is accelerated. Above 1.0 ml/g, the lowering in catalytic performance is small but the crushing strength is insufficient so that the catalysts cannot be used in fixed-bed reactions of hydrocarbons as starting material.

The pore volume and half-volume pore diameter of the shaped catalysts are measured by mercury porosimetry. The mercury porosimetry gives peaks that show pore size distribution of the shaped catalysts. In particular, pores having diameters of approximately 80 to 500 nm ensure a sufficiently high diffusion rate of materials and prevent reduced reaction rate and accelerated coke generation. Accordingly, the shaped catalysts show the highest performance when the pores having these pore volumes account for a major proportion of the total volume of all the pores. In the present invention, the pore diameters are plotted against pore volumes according to mercury porosimetry, and the pore diameter corresponding to half the total integrated pore volume is determined as the half-volume pore diameter.

The zeolites in the invention are not particularly limited and may be any kinds of zeolites. Examples of the zeolites include mordenite, ferrierite, ZSM-4 (omega), ZSM-5 (MFI aluminosilicate), ZSM-11, ZSM-112, ZSM-20, ZSM-22, ZSM-23, ZSM-35, ZSM-48, ZSM-50, X, Y, L and beta.

In the case of aluminosilicate zeolite, the $SiO_2/Al_2O_3$ molar ratio is not influential in the methods of the present invention. The $SiO_2/Al_2O_3$ molar ratio is not substantially limited as long as it is 3 or more. Commercially available zeolites having a desired $SiO_2/Al_2O_3$ molar ratio may be used as they are, or zeolite having an arbitrary composition may be modified to a differing composition by known methods. In detail, a commercially available zeolite having a low $SiO_2/Al_2O_3$ molar ratio may be dealuminized into a zeolite having a higher silica content. Exemplary dealuminization methods are found in Catalysis and Zeolites, Fundamentals and Applications (edited by J. Weitkamp and L. Puppe, Springer, 1999), pp. 127-155, which describes vapor treatment, silicon tetrachloride treatment and hexafluorosilicate treatment. Zeolites treated by these methods may be used in the methods of the present invention.

It is necessary in the invention that the zeolites show acidity. Metal ion-exchanged acidic zeolites as well as protonic zeolites may be used. Examples of the metal ions include alkaline earth metals such as Mg, Ca, Sr and Ba and transition metals such as Fe, Ni, Mn, Co and V. The metal ions and protons may be present together in any ratio. The exchange capacity of the zeolites may be completely replaced by the protons or metals. In the case of excessively high activity, part of the exchange capacity may be replaced by alkali metals such as Li, Na and K at an appropriate proportion to lower the acidity. If more than 90% of the exchange capacity is replaced by the alkali metals, the acidity is excessively lowered, and therefore the replacement of the exchange capacity preferably takes place below this level. Known methods may be adopted to ion-exchange the catalysts with these elements. For example, a protonic zeolite may be ion-exchanged with metal cations, or a zeolite may be impregnated with salt or complex compounds containing these elements.

A third metal next to Si and Al, such as B, Sn, Ga, Mn, Fe or Ti, may be incorporated in the zeolite structure skeleton by known methods to control activity, improve selectivity, prevent coke generation or retard catalyst degradation.

The inorganic binders used in the invention include inorganic compounds including silica, alumina and alumina-silica. Any such inorganic binders may be used unless they adversely affect the reaction catalyzed by the zeolite shaped catalysts.

From the viewpoints of high crushing strength and catalytic performance, the content of inorganic binders in the zeolite shaped catalysts in the invention may be 10 to 40 wt %, preferably 15 to 35 wt %, and more preferably 15 to 30 wt %. The bonding between the inorganic binders and the zeolite affects and sometimes completely deactivates the active sites near the zeolite surface. Accordingly, the content of inorganic binders is preferably as low as possible. However, a low content of inorganic binders is traded off with low crushing strength of the shaped catalyst.

In the present invention, the zeolite shaped catalysts may be obtained by, for example, kneading zeolite powder, an starting material of an inorganic binder, a shaping auxiliary, organic polymer particles having an average diameter of 0.1 to 6 μm and water into a kneaded product, and extruding, drying and calcining the kneaded product.

The zeolite powder may be any zeolite such as alkaline zeolite, ammonium zeolite or protonic zeolite, with alkaline or ammonium zeolite being more preferred. When a protonic zeolite is used, it is preferable that the obtainable kneaded product to be extruded is adjusted to alkaline pH. A protonic zeolite may be used without such adjustment when the acidity of the obtainable kneaded product does not adversely affect the auxiliaries used.

Other than alkaline and ammonium zeolites, zeolites exchanged with metal ions may be used as zeolite powder in the invention. The metal ions herein are all kinds of cations substantially capable of ion exchange, such as Group II metals of the periodic table such as Mg, Ca, Sr and Ba through Group VIII transition metals such as Fe, Ni, Mn, Co and V, and rare earth metals such as La and Ce. These cations may be present together with sodium or ammonium in any proportion. Known methods may be adopted to ion-exchange the catalysts with these elements. For example, a protonic zeolite may be ion-exchanged with metal cations, or a zeolite may be impregnated with salt or complex compounds containing these elements.

The zeolite powder is exchanged with protons or metal ions to show acidity in the course of kneading, calcination and optional treatment such as acid treatment or ion exchange in the shaping process.

Examples of the starting material of an inorganic binder are clay minerals based on smectite swelling clays such as activated clay, bentonite and montmorillonite, or silica sol and alumina sol. Any such materials may be used unless they adversely affect the reaction catalyzed by the zeolite shaped catalysts. In particular, silica powder or silica sol may be preferably used because they usually do not affect the reaction and are excellent in heat stability. Silica as an inorganic binder strongly binds to zeolite crystal particles via dehydration and condensation reaction between the hydroxyl groups on the surface of silica particles and the hydroxyl groups on the surface of zeolite crystal particles. It is considered that silica particles are linked together through similar chemical bonds, and the amorphous silica network having high crushing strength connects the zeolite crystal particles. The silica binder material preferably has smaller particle diameters than the zeolite crystal particles, in which case the silica and zeolite are effectively bound to achieve high crushing strength.

The silica binder materials are not particularly limited, but silica powder and silica sol are preferable. Silica sol is a mixture in which colloidal silica particles are dispersed in water, and alkaline type, ammonium type and acidic type are known. According to the present invention, alkaline or ammonium type silica sol having a pH of 8 to 11 may be preferably used. If the pH is below this range, the binding between the silica binder and the zeolite is weak and the binder can be decomposed depending on the kind of shaping auxiliaries used, failing to fulfill its function. A pH value below 8 results in failure to obtain shaped catalysts having high crushing strength. However, acidic binders may be used when the shaping auxiliaries used are stable in an acidic atmosphere. From the viewpoint of strong crushing strength, the average particle size of the silica powder and silica sol particles is not more than 50 nm, and more preferably not more than 30 nm. The silica binder materials may be synthesized by known methods or may be commercially available as, for example, fumed silica manufactured by Sigma, Snowtex series manufactured by Nissan Chemical Industries, Ltd. and LUDOX colloidal silica manufactured by Grace Davison Co., Ltd.

The shaping auxiliaries used in the invention include thickening agents, dispersants, surfactants, deflocculants, water retention agents and organic binders. These shaping auxiliaries usually have several functions but are collectively referred to as such in the invention for the sake of convenience. They may be used singly, or several kinds may be used in combination. The auxiliaries help the zeolite and the inorganic binders be dispersed homogeneously and bind together, and also adjust the viscosity of the kneaded product to an extrudable level.

Exemplary shaping auxiliaries are organic compounds, synthetic resins giving specific functions, gums, naturally-occurring polymers and mixtures thereof. The shaping auxiliaries are burnt and evaporated in the calcination step subsequent to the extrusion and do not remain in the final zeolite shaped catalysts. Examples of the auxiliaries include methyl cellulose, carboxymethyl cellulose, hydroxyethyl cellulose, polyethylene glycol, polyethylene oxide, polyacrylamide, polypropylene glycol alginate, polyvinylpyrrolidone, polyurethane, xanthan gum, and copolymers and derivatives thereof. At least one auxiliary selected from the above compounds may be suitably used. In particular, at least one selected from urethane-modified polyethylene glycol, polypropylene glycol alginate, water-soluble polyurethane produced by a method described in JP-A-2004-169011, polyethylene oxide, methyl cellulose, xanthan gum and derivatives thereof is preferably used, in which case the strength of the shaped products is greatly improved. The shaping auxiliaries may be synthesized by known methods, or commercially available auxiliaries may be used.

The total weight of the shaping auxiliaries used in the invention may be not more than 15 wt % and not less than 2 wt %, and preferably not more than 10 wt % and not less than 2 wt % relative to the weight of zeolite. The shaping auxiliaries are evaporated and burnt in the calcination step, thereby creating pores. The size of the pores is influenced by properties of the shaping auxiliaries, and all sizes do not provide good effects for the improvement of shaped catalyst performance. Therefore, using the shaping auxiliaries in amounts exceeding the above range leads to an increased number of pores having undesired sizes, resulting in lowered performance of the shaped catalysts.

Examples of the organic polymer particles include silicone rubbers, silicone resins, polystyrenes, crosslinked polystyrenes, polystyrene resins, styrene/divinylbenzene copolymers, styrene/acrylic acid copolymers, styrene/acrylate copolymers, styrene/acrylonitrile copolymers, styrene/methacrylic acid copolymers, styrene/methacrylate copolymers, styrene/methacrylonitrile copolymers, polyvinyltoluenes, polyethylenes, polyolefin resins, acrylic resins, crosslinked acrylic resins, ethylene/acrylic acid copolymers, ethylene/acrylate copolymers, ethylene/acrylonitrile copolymers, ethylene/methacrylic acid copolymers, ethylene/methacrylate copolymers, ethylene/methacrylonitrile copolymers, polymethyl methacrylates, polyethyl methacrylates, polyglycidyl methacrylates, crosslinked polymethyl methacrylates, polyacrolein, polyglutaraldehyde, polyacrylamide, crosslinked alcoholic resins, phenolic resins, epoxy resins, nylon 6, nylon 66, nylon 11, nylon 12, benzoguanamine resins, melamine resins, melamine/guanamine resins and poly-n-butyl acrylate. At least one selected from the above compounds may be used in the invention.

In particular, favorable results are obtained by using polystyrenes, crosslinked polystyrenes, polystyrene resins, styrene/divinylbenzene copolymers, styrene/acrylic acid copolymers, styrene/acrylate copolymers, styrene/acrylonitrile copolymers, styrene/methacrylic acid copolymers, styrene/methacrylate copolymers, styrene/methacrylonitrile copolymers, polymethyl methacrylates, polyethyl methacrylates, polyglycidyl methacrylates and crosslinked polymethyl methacrylates.

The organic polymer particles may be easily obtained commercially in the form of powder, slurry, latex or emulsion.

Exemplary commercially available products include MUTICLE series manufactured by Mitsui Chemicals, Inc., GLOSSDELL series manufactured by Mitsui Chemicals, Inc., JULIMER series manufactured by Nihon Junyaku Co., Ltd., and polystyrene particle series manufactured by Seradyn Inc. Alternatively, the organic polymers described above maybe synthesized by known methods. Polymerization processes to produce the organic polymers are not limited in the present invention, and synthetic organic polymers produced by any methods may be used. In particular, emulsion polymerization gives polymers having narrow particle size distribution, and methods as described in JP-A-S59-59741 and JP-A-H03-140286 may be preferably adopted.

The organic polymer particles used in the invention are fine particles having diameters of 0.1 to 6 μm, and preferably 0.2 to 5 μm. If the particle diameter is less than 0.1 μm, pores formed in the shaped catalyst will be so small that the diffusion within the shaped catalyst is not sufficiently easy. Such catalysts have a short life because of high coking rate. The use of organic polymer particles having diameters larger than 6 μm leads to lower crushing strength. The particles may have various shapes such as spheres, flakes, flat particles and elliptic particles, with spherical particles being particularly preferable. The organic polymer particles are burnt and evaporated in the calcination step in the production of zeolite shaped catalysts, whereby pores similar in size to the particles are formed in the shaped catalysts. By using the organic polymer particles with the above particle size, the pores formed have favorable sizes. When the organic polymer particles used have narrow particle size distribution, pores having similar sizes are predominantly formed. In general, the comparison of shaped catalysts having identical pore volumes shows that shaped catalysts having a narrow pore size distribution with a large number of similar-size pores exhibit higher crushing strength than shaped catalysts having a wider pore size distribution.

The diameter of the organic polymer particles may be easily determined from electron micrographs.

The amount of the organic polymer particles in the invention may be 10 to 60%, and more preferably 10 to 50% relative to the weight of zeolite. Below this range, pores formed by the evaporation and burning of the organic polymer particles have a small total volume, and the obtainable shaped catalyst cannot perform sufficiently. Amounts exceeding the above range lead to lower crushing strength of the shaped catalysts.

In the invention, the usage amount of water is adjusted such that the weight ratio of the total water content in the mixture relative to the whole mixture is in the range of 20 to 60%, and preferably 25 to 50%. Below this range, the viscosity is so high that shaping is infeasible. If the water content exceeds the above range, the obtainable shaped products have low crushing strength and cannot be used as industrial catalysts. The water content is an important factor that influences not only the easiness of shaping but also the pore volume and pore size of the zeolite shaped catalysts.

In a preferred embodiment of the invention, the zeolite shaped catalyst is prepared by kneading a mixture that contains 100 parts by weight of the zeolite powder, 10 to 70 parts by weight of the starting material of an inorganic binder, not more than 15 parts by weight of the shaping auxiliary, 10 to 60 parts by weight of the organic polymer particles having an average diameter of 0.1 to 6 μm, and 20 to 60% of water relative to the total weight of the mixture, and extruding, drying and calcining the kneaded product.

The mixture containing the above amounts of the zeolite, starting material of an inorganic binder, shaping auxiliary, organic polymer particles and water is kneaded into an extrudable kneaded product. The kneading is carried out at or above room temperature to give a kneaded product in an appropriate clay-like state. The kneaded product is shaped with an extruder and is dried. The drying conditions are not particularly limited, but the drying may be preferably carried out in an atmosphere or flow of air or nitrogen, preferably at 50 to 120° C. Subsequent to the drying step, the shaped product is calcined in the presence or flow of an oxygen-containing gas at temperatures not less than 400° C., and preferably in the range of 500 to 600° C. In the calcination step, the temperature is increased at a low rate in the beginning and then brought to a desired temperature in order to prevent rapid changes in the shaped products. In the course of calcination, the inorganic binder and the zeolite bind together, and the organic composition of the shaping auxiliary and organic polymer particles is burnt and evaporated to afford the target zeolite shaped catalyst.

The diameter of the zeolite shaped catalyst may be in the range of 0.5 to 3 mm. Below this range, the pressure loss in the use of the catalyst is large and causes coke generation. Diameters greater than the above range lead to lower catalytic performance.

Some reactions to be catalyzed by the shaped catalysts may require that the alkalis or metal components contained in the shaped catalysts should be removed. In this case, the shaped catalysts are washed after such metal components are removed. For the washing, aqueous solutions of hydrochloric acid or nitric acid are preferably used because they can be removed by the subsequent drying and calcining steps and do not remain in the shaped catalysts.

In another aspect of the invention, hydrocarbons are converted using the zeolite shaped catalyst manufactured by the foregoing process. As will be described later, the methods of the invention are suitably used for fixed-bed reaction processes.

The reaction processes according to the invention are not particularly limited. A preferred reaction is a conversion reaction of hydrocarbons which generally produces cokes at high rates, in detail, catalytic cracking of hydrocarbon materials containing olefins into olefins that are lower than the hydrocarbon materials.

Examples of the hydrocarbon conversion reactions include catalytic cracking of paraffins, and catalytic cracking of olefins.

The hydrocarbon conversion methods according to the present invention may be carried out with any reactor systems such as fixed bed, fluidized bed and moving bed. Fixed-bed reactors are preferable because the crushing strength required of the zeolite shaped catalysts may be relatively low and the reactor equipment is simple. The zeolite shaped catalyst is packed in such reactor and an olefin-containing hydrocarbon material is supplied thereto and is converted.

Examples of the hydrocarbons include methane, ethane, propane, n-butane, isobutane, linear, branched or cyclic pentane, linear, branched or cyclic hexane, linear, branched or cyclic heptane and linear, branched or cyclic octane. Aromatic hydrocarbons such as benzene, toluene and xylene are also employable. Examples of the olefins include 1-butene, cis-2-butene, trans-2-butene, isobutene, 1-pentene, cis-2-pentene, trans-2-pentene, 2-methyl-1-butene, 2-methyl-2-butene, 3-methyl-1-butene, cyclopentene, 1-hexene, 2-hexene, 3-hexene, methylbutenes, dimethylbutenes, neohexene, cyclohexene, methylcyclopentene, linear heptenes, branched heptenes, cyclic heptenes, methylcyclohexenes, and linear, branched or cyclic olefins having 9 to 12 carbon atoms.

With the zeolite shaped catalysts of the invention, dienes such as butadiene and cyclopentadiene do not lower catalytic activity. Even if the hydrocarbon material contains diene components such as butadiene at approximately up to 2 wt % relative to the weight of the hydrocarbon material, the catalysts of the invention provide a stable propylene yield over long periods with a small increase in coke generation rate as long as the diene amount is at such levels.

The materials containing such components are for example: a fraction (a raffinate-1) that is obtained after butadiene is extracted and removed from a fraction (a crude C4 fraction) obtained from the top of a debutanizer, to which a mixture obtained in a naphtha thermal cracking furnace or a naphtha catalytic cracking furnace is sent after separating C1 to C3 fractions from the mixture; an olefin fraction containing no diene components that is obtained by selectively catalytically hydrogenating the crude C4 fraction without extraction; a fraction (a raffinate-2) that remains after isobutene is removed from the raffinate-1; a fraction that remains after isoprene is extracted and removed from a fraction (a crude C5 fraction) obtained from the bottom of a debutanizer; an olefin fraction containing no diene components that is obtained by selectively catalytically hydrogenating the crude C5 fraction without extraction; and an olefin fraction containing no diene components that is obtained by selectively catalytically hydrogenating a fraction obtained from the top of a depentanizer, to which a mixture obtained in a naphtha thermal cracking furnace or a naphtha catalytic cracking furnace is sent after separating C1 to C3 fractions from the mixture. In addition, various fractions obtained in FCC processes that contain olefins, paraffins and aromatics and are not used as gasoline or the like may be used. These materials may be used singly or may be mixed together in an appropriate ratio. The materials are not limited to those described above.

The present invention is directed to catalytic cracking of olefin-containing hydrocarbon materials into olefins that are lower than the hydrocarbon materials. In particular, the methods of the invention are suitably applied to catalytic cracking of hydrocarbon materials containing C4-12 olefins into ethylene and propylene.

In an embodiment, the olefin-containing hydrocarbon materials contain at least one C4-12 olefin and 10 to 60 wt % of at least one C1-12 saturated hydrocarbon.

The catalytic cracking temperature is in the range of 400 to 580° C., preferably 480 to 580° C., and more preferably 480 to 560° C. If the reaction temperature is below this range, it is not preferable, since the conversion of the olefins is lowered and the productivity of ethylene and propylene is insufficient. If the reaction temperature exceeds the above range, coke generation is accelerated and the catalysts reduce activity quickly.

The catalytic cracking pressure is in the range of 0.05 to 2 MPa, preferably 0.05 to 1 MPa, and more preferably 0.05 to 0.5 MPa.

The weight hourly space velocity (WHSV) of the hydrocarbon material per unit catalyst weight is in the range of 20 to 256 $hr^{-1}$, preferably 32 to 256 $hr^{-1}$, and more preferably 40 to 128 $hr^{-1}$. When the weight hourly space velocity (WHSV) is below this range, the pentene content in the obtainable fractions can be reduced and the rate of decrease of the catalytic activity is retarded to some extent. However, the yields of hydrogen, saturated hydrocarbons and aromatic hydrocarbons are increased at the same time, and high selectivity and productivity of ethylene and propylene cannot be obtained. If the weight hourly space velocity (WHSV) exceeds the above range, coke generation is accelerated. Therefore, WHSV above the range is not preferable.

A single reactor or a plurality of reactors may be used. In the case of plural reactors, a serial arrangement of the reactors permits controlling reaction conditions more precisely. A parallel arrangement allows for constant production by switching catalytic cracking in one reactor and catalyst regeneration in other reactor. These reaction conditions described hereinabove allow for maximum selectivity, yield and productivity of propylene and prevent generation of cokes that can lower catalytic activity.

When a single reactor is used, olefins of 4 or more carbon atoms including pentene may be separated from the fraction obtained and be recycled into the catalytic cracking reactor and reused together with a fresh feed. Alternatively, the olefins of 4 or more carbon atoms that are separated may be fed to a naphtha cracker together with a fresh naphtha feed.

EXAMPLES

The present invention will be described in detail hereinbelow without limiting the scope of the invention.

Properties of shaped catalysts were evaluated by the following methods.

(1) Crushing Strength

A Kiya-type hardness meter was used. This hardness meter was designed to apply load on a shaped catalyst. The load which caused catalyst fracture was obtained as crushing strength (kg). Five pieces of shaped catalysts were tested, and the average thereof was adopted.

(2) Pore Volume

The pore volume was measured by mercury porosimetry.

(3) Half-Volume Pore Diameter

The half-volume pore diameter was obtained by reading out a pore diameter which corresponded to half the total pore volumes in plots of pore diameters versus integrated pore volume obtained by the mercury porosimetry.

(4) Diameter of Organic Polymer Particles

Diameters of organic polymer particles were measured with an electron microscope.

Example 1

In a mortar, there were kneaded for 10 minutes 10 g of commercially available powdery ammonium salt-type ZSM-5 ($SiO_2/Al_2O_3$ molar ratio: 500), 5.8 g of a sodium silica sol (Snowtex S, manufactured by Nissan Chemical Industries, Ltd., silica: 30%, particle diameters: 8 to 11 nm), 0.20 g of a water-soluble polyurethane resin produced by a method described in JP-A-2004-169011 (Example 1), 0.20 g of xanthan gum, 1.5 g of a polystyrene resin (average particle diameter: 0.8 μm) produced by a method described in JP-A-H03-140286 (Polymerization Example 1) and 4.0 g of water. The resultant clay-like paste was extruded into a shaped body 1.5 mm in diameter by means of an extruder. The shaped body was air-dried overnight, dried at 120° C. for 1.5 hours, and calcined in an air flow at 500° C. for 5 hours. The calcined body was soaked in a 1N aqueous nitric acid solution under reflux for 3 hours, then filtered and washed with water. The nitric acid treatment, filtration and washing with water were repeated three times, and the shaped body was dried and was calcined in air at 500° C. for 5 hours. Measurement with a Kiya-type hardness meter resulted in an average crushing strength of 1.0 kg. Mercury porosimetry resulted in a pore volume of 0.55 ml/g and a half-volume pore diameter of 177 nm.

The shaped catalyst was broken to approximately 2 mm in length and was evaluated in terms of performance as a catalyst for catalytic cracking of a C4 fraction material. A fixed-bed flow reactor (inner diameter: 10.7 mm, length: 250 mm) was used for the reaction. A quartz tube was packed with 0.7 g of the shaped catalyst, together with quartz wool and quartz sand as holding materials, so that the total length of the packings became 250 mm. The quartz tube was mounted in the reactor. While the temperature of the catalyst layer was maintained at 550° C., a C4 fraction starting material obtained by naphtha cracking was supplied at a flow rate of 30 g/h (WHSV=43 hr$^{-1}$) and was catalytically cracked at a reaction pressure of 0.05 MPa. The product that flowed out was maintained in the gas state and was analyzed by gas chromatography.

The results are shown in Table 1.

The conversion of the starting material, the product yield and the catalyst life were calculated by the following equations.

Conversion (%)=(1−(weight of unreacted butene)/ (weight of butene in the starting material))×100   (1)

Catalyst life=time on stream when "(initial conversion)−(conversion)" reached 10%   (2)

Yield [ethylene ($C_2^=$)+propylene ($C_3^=$)](%)=(weight of $C_2^=$+$C_3^=$ produced)/(weight of butene in the starting material))×100   (3)

Examples 2 and 3

Shaped catalysts were produced under the same conditions as in Example 1 and were used in catalytic cracking reaction of a C4 fraction material, except that the sodium silica sol was used in 8.2 g, that the polystyrene resin was used in 2.0 g or 3.0 g respectively, and that water was used in 4.8 g or 4.0 g respectively. The results are shown in Table 1.

Examples 4 to 6

Shaped catalysts were produced under the same conditions as in Example 2 and were used in catalytic cracking reaction of a C4 fraction material, except that a polystyrene resin having an average particle diameter of 0.5 μm was used in 1.0 g, 2.0 g or 3.0 g respectively, and that water was used in 3.5 g. The results are shown in Table 1.

Example 7

A shaped catalyst was produced under the same conditions as in Example 2 and was used in catalytic cracking reaction of a C4 fraction material, except that the polystyrene resin was replaced by 4.4 g of a polystyrene emulsion (polystyrene: 45%, average particle diameter: 0.65 μm), and that water was used in 3.0 g. The results are shown in Table 1.

Example 8

A shaped catalyst was produced under the same conditions as in Example 1 and was used in catalytic cracking reaction of a C4 fraction material, except that the zeolite was used in 4.7 g, that the polystyrene resin was replaced by 1.0 g of polymethyl methacrylate (PMMA, product name: JULIMER MB-SX manufactured by Nihon Junyaku Co., Ltd., average particle diameter: 4-5 μm), and that water was used in 4.3 g. The results are shown in Table 1.

Example 9

A shaped catalyst was produced under the same conditions as in Example 2 and was used in catalytic cracking reaction of a C4 fraction material, except that the xanthan gum was replaced by 0.2 g of polypropylene glycol alginate (manufactured by JUNSEI CHEMICAL Co., LTD.), that the polystyrene resin was used in 2.0 g, and that water was used in 4.8 g. The results are shown in Table 1.

Example 10

A shaped catalyst was produced under the same conditions as in Example 2 and was used in catalytic cracking reaction of a C4 fraction material, except that the sodium silica sol was used in 14 g, that the water-soluble urethane was used in 0.25 g, that the xanthan gum was used in 0.25 g, and that water was not used. In this example, the silica sol contained much water and addition of water was not necessary. The results are shown in Table 1.

Example 11

In a kneader, there were kneaded for 30 minutes 30 g of commercially available powdery ammonium salt-type ZSM-5 ($SiO_2/Al_2O_3$ molar ratio: 500), 24.6 g of a sodium silica sol (Snowtech S, manufactured by Nissan Chemical Industries, Ltd., silica: 30%, particle diameters: 8 to 11 nm), 0.60 g of a water-soluble polyurethane resin produced by a method described in JP-A-2004-169011 (Example 1), 0.6 g of polypropylene glycol alginate (manufactured by JUNSEI CHEMICAL Co., LTD.), 4.5 g of a polystyrene resin (average particle diameter: 0.8 μm) produced by a method described in JP-A-H03-140286 (Polymerization Example 1) and 10.5 g of water. The resultant clay-like paste was extruded into a shaped body 1.5 mm in diameter by means of an extruder. The shaped body was air-dried overnight, dried at 120° C. for 1.5 hours, and calcined in an air flow at 500° C. for 5 hours. The calcined body was soaked in a 1N aqueous nitric acid solution under reflux for 3 hours, then filtered and washed with water. The nitric acid treatment, filtration and washing with water were repeated three times, and the shaped body was dried and was calcined in air at 500° C. for 5 hours. Measurement with a Kiya-type hardness meter resulted in an average crushing strength of 1.1 kg. Mercury porosimetry resulted in a pore volume of 0.62 ml/g and a half-volume pore diameter of 294 nm.

The shaped catalyst was evaluated in terms of performance as a catalyst for catalytic cracking of a C4 fraction material under the same conditions as in Example 1. The results are shown in Table 1.

Example 12

A shaped catalyst was produced under the same conditions as in Example 11 and was used in catalytic cracking reaction of a C4 fraction material, except that the polypropylene glycol alginate was replaced by 0.90 g of xanthan gum, that the polystyrene resin was used in 6.0 g, and that water was used in 7.5 g. The results are shown in Table 1.

Comparative Example 1

A shaped catalyst was produced under the same conditions as in Example 1 and was used in catalytic cracking reaction of a C4 fraction material, except that the sodium silica sol was used in 3.6 g, that the water-soluble polyurethane resin according to JP-A-2004-169011 (Example 1) was used in 0.1 g, that the xanthan gum was used in 0.1 g, that water was used in 5.0 g, and that the polystyrene resin was not used. The shaped catalyst having this low content of silica binder had a crushing strength of only 0.8 kg. The results are shown in Table 1.

Comparative Examples 2 to 4

Shaped catalysts were produced under the same conditions as in Comparative Example 1 and was used in catalytic cracking reaction of a C4 fraction material, except that the zeolite was used in 5 g, 10 g or 10 g respectively, that the sodium silica sol was used in 2.9 g, 8.2 g or 14.0 g respectively, that the water-soluble polyurethane resin was used in 0.05 g, 0.20 g or 0.25 g respectively, that the xanthan gum was used in 0.05 g, 0.20 g or 0.25 g respectively, and that water was used in 2.5 g, 1.8 g or 0 g respectively. These shaped catalysts containing no organic polymer particles had insufficient pore volumes and half-volume pore diameters, and the catalytic life thereof was short. The results are shown in Table 1.

TABLE 1

(Examples and Comparative Examples)

| | \multicolumn{7}{c}{Mixtures for shaping} | | |
|---|---|---|---|---|---|---|---|---|
| | Zeolite | Silica sol | Shaping auxiliaries and amounts | | Porosifiers, average particle diameters and amounts | | | Water added | Total weight |
| | g | g | g | | g | | μm | g | g | g |
| Ex. 1 | 10 | 5.8 | Water-soluble PU | 0.20 | Xanthan gum | 0.20 | Polystyrene resin | 0.8 | 1.5 | 4.0 | 22 |
| Ex. 2 | 10 | 8.2 | Water-soluble PU | 0.20 | Xanthan gum | 0.20 | Polystyrene resin | 0.8 | 2.0 | 4.8 | 25 |
| Ex. 3 | 10 | 8.2 | Water-soluble PU | 0.20 | Xanthan gum | 0.20 | Polystyrene resin | 0.8 | 3.0 | 4.0 | 26 |
| Ex. 4 | 10 | 8.2 | Water-soluble PU | 0.20 | Xanthan gum | 0.20 | Polystyrene resin | 0.5 | 1.0 | 3.5 | 23 |
| Ex. 5 | 10 | 8.2 | Water-soluble PU | 0.20 | Xanthan gum | 0.20 | Polystyrene resin | 0.5 | 2.0 | 3.5 | 24 |
| Ex. 6 | 10 | 8.2 | Water-soluble PU | 0.20 | Xanthan gum | 0.20 | Polystyrene resin | 0.5 | 3.0 | 3.5 | 25 |
| Ex. 7 | 10 | 8.2 | Water-soluble PU | 0.20 | Xanthan gum | 0.20 | Polystyrene emulsion | 0.65 | 4.4 | 3.0 | 26 |
| Ex. 8 | 10 | 4.7 | Water-soluble PU | 0.20 | Xanthan gum | 0.20 | Crosslinking PMMA | 4.0 | 1.0 | 4.3 | 20 |
| Ex. 9 | 10 | 8.2 | Water-soluble PU | 0.20 | PPG alginate | 0.20 | Polystyrene resin | 0.8 | 2.0 | 4.8 | 25 |
| Ex. 10 | 10 | 14.0 | Water-soluble PU | 0.25 | Xanthan gum | 0.25 | Polystyrene resin | 0.8 | 2.0 | 0 | 27 |
| Ex. 11 | 30 | 24.6 | Water-soluble PU | 0.60 | PPG alginate | 0.60 | Polystyrene resin | 0.8 | 4.5 | 10.5 | 71 |
| Ex. 12 | 30 | 24.6 | Water-soluble PU | 0.90 | Xanthan gum | 0.90 | Polystyrene resin | 0.8 | 6.0 | 7.5 | 70 |
| Comp. Ex. 1 | 10 | 3.6 | Water-soluble PU | 0.10 | Xanthan gum | 0.10 | | | | 5.0 | 19 |
| Comp. Ex. 2 | 5 | 2.9 | Water-soluble PU | 0.05 | Xanthan gum | 0.05 | | | | 2.5 | 10 |
| Comp. Ex. 3 | 10 | 8.2 | Water-soluble PU | 0.20 | Xanthan gum | 0.20 | | | | 1.8 | 20 |
| Comp. Ex. 4 | 10 | 14.0 | Water-soluble PU | 0.25 | Xanthan gum | 0.25 | | | | 0 | 25 |

| | Properties of shaped catalysts | | | | Catalyst performance | | | |
|---|---|---|---|---|---|---|---|---|
| | Binder content wt % | Crushing strength kg | Half-volume pore diameter nm | Pore volume ml/g | Butene weight percent in the starting material wt % | Conversion % | $C_2^= + C_3^=$ yield % | Life hr |
| Ex. 1 | 15 | 1.0 | 177 | 0.55 | 46 | 71 | 43 | 90 |
| Ex. 2 | 20 | 1.5 | 185 | 0.57 | 49 | 73 | 42 | 100 |
| Ex. 3 | 20 | 0.9 | 270 | 0.68 | 45 | 72 | 46 | 110 |
| Ex. 4 | 20 | 1.6 | 82 | 0.40 | 49 | 70 | 44 | 80 |
| Ex. 5 | 20 | 1.8 | 118 | 0.52 | 50 | 72 | 44 | 100 |
| Ex. 6 | 20 | 1.2 | 153 | 0.64 | 50 | 73 | 44 | 100 |
| Ex. 7 | 20 | 1.1 | 227 | 0.62 | 48 | 72 | 45 | 110 |
| Ex. 8 | 12 | 1.3 | 104 | 0.47 | 50 | 72 | 41 | 90 |
| Ex. 9 | 20 | 1.0 | 235 | 0.70 | 50 | 75 | 44 | 100 |
| Ex. 10 | 30 | 2.4 | 100 | 0.41 | 50 | 70 | 41 | 85 |
| Ex. 11 | 20 | 1.1 | 294 | 0.62 | 58 | 71 | 40 | 82 |
| Ex. 12 | 20 | 1.2 | 220 | 0.59 | 57 | 71 | 44 | 92 |
| Comp. Ex. 1 | 10 | 0.8 | 112 | 0.45 | 63 | 72 | 37 | 75 |
| Comp. Ex. 2 | 15 | 2.2 | 76 | 0.33 | 61 | 70 | 35 | 57 |
| Comp. Ex. 3 | 20 | 4.4 | 64 | 0.28 | 47 | 69 | 37 | 55 |
| Comp. Ex. 4 | 30 | 4.2 | 58 | 0.21 | 46 | 66 | 36 | 50 |

[Remarks]
Water-soluble PU: water-soluble polyurethane
PPG Alginate: polypropylene glycol alginate

The invention claimed is:

1. A hydrocarbon conversion method comprising catalytically cracking hydrocarbon starting material containing olefins into olefins that are lower than the starting material with use of a zeolite shaped catalyst, the zeolite shaped catalyst being obtained by kneading zeolite powder, a starting material of an inorganic binder, shaping auxiliary (ies) organic polymer particles having an average diameter of 0.1 to 6 μm and water into a kneaded product, and extruding, drying and calcining the kneaded product.

2. A hydrocarbon conversion method comprising catalytically cracking hydrocarbon starting material containing olefins into olefins that are lower than the starting material with use of a zeolite shaped catalyst, the zeolite shaped catalyst comprising zeolite and an inorganic binder and being obtained by kneading zeolite powder, a starting material of an inorganic binder, shaping auxiliary(ies), organic polymer particles having an average diameter of 0.1 to 6 μm and water into a kneaded product, and extruding, drying and calcining the kneaded product, the zeolite shaped catalyst having a zeolite component content of not less than 60 wt % relative to the total weight, a pore volume of 0.4 to 1.0 ml/g, a half-volume pore diameter of 80 to 500 nm and a crushing strength of not less than 0.9 kg.

3. The hydrocarbon conversion method according to claim 1 or claim 2, wherein the zeolite is MFI zeolite.

4. The hydrocarbon conversion method according to claim 1 or claim 2, wherein the content of the inorganic binder is not more than 40 wt % relative to the total weight of the zeolite shaped catalyst.

5. The hydrocarbon conversion method according to claim 1 or claim 2, wherein the inorganic binder is silica.

6. The hydrocarbon conversion method according to claim 1 or 2, wherein the amounts are 100 parts by weight for the zeolite powder, 10 to 70 parts by weight for the inorganic binder material, not more than 15 parts by weight for the starting materials of the inorganic binder, not more than 15 parts by weight for the shaping auxiliary(ies), 10 to 60 parts by weight for the organic polymer particles having an average diameter of 0.1 to 6 μm, and 20 to 60% for water relative to the total weight of the kneaded product.

7. The hydrocarbon conversion method according to claim 1 or 2, wherein the zeolite powder is ammonium zeolite or alkaline zeolite.

8. The hydrocarbon conversion method according to claim 1 or 2, wherein the starting material of inorganic binder is a silica sol or a sodium silica sol.

9. The hydrocarbon conversion method according to claim 1 or 2, wherein the hydrocarbon starting material containing olefins contains at least one C4-12 olefin and 10 to 60 wt % of at least one C1-12 saturated hydrocarbon, wherein the olefins that are lower than the starting material are ethylene and propylene, and wherein the catalytic cracking temperature is in the range of 400 to 580° C.

10. The hydrocarbon conversion method according to claim 9, wherein the catalytic cracking pressure is in the range of 0.05 to 2 MPa and the weight hourly space velocity (WHSV) of the hydrocarbon starting material per unit catalyst is in the range of 20 to 256 $hr^{-1}$.

* * * * *